United States Patent [19]

Burton

[11] Patent Number: 5,095,023

[45] Date of Patent: Mar. 10, 1992

[54] METHOD OF SHORTENING EFFECTIVE TIME OF ANAESTHETIC

[76] Inventor: Henry J. Burton, 19637 Greenhaven, Covina, Calif. 91724

[21] Appl. No.: 706,350

[22] Filed: May 28, 1991

[51] Int. Cl.$^5$ .......................................... A61K 31/455
[52] U.S. Cl. ................................................. 514/356
[58] Field of Search ........................................ 514/356

[56] References Cited

PUBLICATIONS

Tsuji, et al, Preparation of azacycloakane derivatives as absorption promoters, CA 108(19):167333w, 1987.
Uchida, et al, Effects of anti-anginal agents on cyclic reductions of coronary blood flow, CA 91(15):117312y, 1978.

Primary Examiner—Marianne Cintins
Assistant Examiner—Rebecca Cook
Attorney, Agent, or Firm—Boniard I. Brown

[57] ABSTRACT

A method for reducing residual numbness experienced by dental and medical patients infiltration injection in the gums or mouth region with anaesthetic. After a dental or medical procedure, such as filling or extracting a tooth, a quantity of niacin is placed against the gum or other area where the anaesthetic was initially injected. The niacin enters the blood vessel walls to expand the blood vessels, thus to effect an increased flow of blood for more rapid transport of anaesthetic from the numbed area.

8 Claims, No Drawings

METHOD OF SHORTENING EFFECTIVE TIME OF ANAESTHETIC

BACKGROUND AND SUMMARY OF THE INVENTION

This invention relates to a method of reducing prolonged numbness experienced by dental and medical patients after being injected with local infiltration anaesthetic to reduce the pain associated with procedures such as drilling, removing a tooth, mouth surgery, or other treatments.

In order to drill into or pull a decayed or infected tooth or perform work on gums or muscles in the mouth, it is a common practice to first inject a quantity of anaesthetic, such as liquid Novocain, Carbocaine, lidocaine or other appropriate anaesthetic into the mouth tissue at the gum area surrounding the tooth. The injected anaesthetic reduces the pain associated with the drilling or pulling process. Epinephrine may also be included with the anaesthetic to reduce or stop bleeding.

The injected anaesthetic produces a numbness or lack of feeling that often lasts for a period longer than necessary for treatment and up to about three hours afterward. The present invention concerns a procedure to reduce the period of numbness from about three hours down to approximately one-half hour. In carrying out the invention, the dentist places a tablet of essentially pure niacin (vitamin B3) in the patient's mouth and against the gum area where the anaesthetic was injected. This placement of the tablet takes place only after the dentist or physician has finished the work or treatment. The drilling, filling, surgery, etc., are carried out in conventional fashion prior to placement of the niacin tablet against the numbed area.

Niacin is known to be a vasodilator and serves to widen or enlarge vessels and capillaries that carry blood within the human body. When a niacin tablet is placed against a gum or other area previously injected with anaesthetic, it is believed that the niacin contacts and enlarges the blood vessels in the numbed area, so that the flow of blood through the numbed area is thereby increased, whereby the blood is better enabled to carry the anaesthetic away from the numbed area. New blood replaces the anaesthetic-carrying blood so that after a relatively short period of time the patient no longer experiences the numb feeling.

It is necessary that the niacin remain in contact with the previously numbed area of the mouth for a sufficient time to expand the blood vessels and maintain them in an expanded condition while new blood is replacing the anaesthetic-absorbed blood. Usually, the patient has to hold the niacin tablet against the number area for the time required for it to dissolve, usually at least 10 minutes. After the niacin tablet is dissolved, its effect on the blood vessels continues, because some niacin in solution form remains in the blood stream for a short time.

The niacin is preferably applied to the anaesthetic-numbed area in the form of a flat tablet, disk pellet, gel or strips, having a weight which may vary from about 25 to 1000 milligrams, depending on the weight of the patient and other factors hereinafter mentioned. Thus, for a small child with the factors mentioned below relatively minimal, 25 milligrams might be sufficient, whereas a heavy, elderly person, with other factors adverse, might require several hundred milligrams. The tablet is essentially pure niacin, although a small quantity of flavoring or filling may be compounded with the niacin to improve its taste or to form tablets. When the niacin tablet is placed in the patient's mouth (against the gum), the saliva in the mouth dissolves the powdered niacin, and niacin in solution form is carried into the blood vessel walls on or near the gum surface.

The effect of the anaesthetic will vary somewhat, depending on such factors as the quantity and anaesthetic injected, the patient's size (weight) and age, the person's normal blood flow rate, the condition of the patient's blood vessels, and the quantity of any epinephrine which may have been injected to contract blood vessels.

In actual practice of the invention, it has been found that numbness produced by the injection of anaesthetics into a patient's gum or mouth area persists for about three hours or more without application of niacin to the numbed area. When a niacin tablet weighing about 135 milligrams is applied to the numbed area for about ten minutes, the numbed condition persists only for about forty-five minutes or less. When a 100 milligram tablet is applied to an older person weighing 150 pounds, the numbed condition has been found to last about one-half hour. The persistence time of the numbed condition will vary, depending upon the absorbtion, blood vessels, condition of the patient, weight of the patient, age, and the amount of any epinephrine previously injected.

Although the preferred method of administering the niacin is in the form of tablets, it may also be incorporated into small flat pads, disks or strips. For example, a small cloth disk having several layers of cloth sewn together can be soaked in a saturated niacin solution and dried. The niacin-impregnated cloth disk can be placed within the patient's mouth against the numbed area to reduce the duration of the numbness experienced by the patient. If the quantity of niacin in the cloth disk is not sufficient to fully remove the numbed feeling within the expected time, then a second niacin-impregnated disk may be placed in the patient's mouth to continue the treatment.

Use of niacin as an agent to reduce numbness due to anaesthetic injections is believed to be new in the art. According to an article appearing in "Pharmaceutical Science" for 1975 (15th edition), niacin has been used in the treatment of pellagra, and as a dietary supplement for alleviating such conditions as weight loss, skin rash, physical weakness, and mental nervousness. In an article appearing at page 1557 in "The pharmacological Basis of Therapeutics" edited by Goodman & Gilman, and published by Macmillan Publishing Co. in 1980, it is stated that niacin has been used as a vasodilator and as an agent to lower plasma cholesterol. Niacin is apparently considered to be a vitamin, i.e., a compound required in tiny amounts in the human diet for proper biological functioning and good health. An article appearing at page 877 in "Drug Information for the Consumer", published in 1989 by Consumers' Union in Mount Vernon, New York, indicates that the recommended dietary allowance for niacin is 18 milligrams per day for adult males and 13 milligrams per day for adult females. the use of niacin in the present invention is deemed to be new in the art relating to the reduction in numbness resulting from injection of anaesthetic.

Thus there has been shown and described a noval method of shortening effective time of anaesthetic which fulfills all the objects and advantages sought therefor. Many changes, modifications, variations and other uses and applications of the subject invention will, however, become apparent to those skilled in the art after considering this specification together with the accompanying claims. All such changes, modifications, variations and other uses and applications which do not depart from the spirit and scope of the invention are deemed to be covered by the invention which is limited only by the claims which follow.

The inventor claims:

1. A method of reducing the time duration of numbness felt by a patient following the injection of anaesthetic by infiltration into the patient's mouth or gum tissue, said method comprising:

providing a mass of 25 to 1000 milligrams niacin, and placing and dissolving the niacin mass against the internal mouth surface where the anaesthetic was injected.

2. A method according to claim 1, wherein:

the niacin is in the form of essentially pure niacin weighing 100 to 125 milligrams.

3. A method according to claim 1, wherein:

the niacin is applied as a coating on a cloth pad that is inserted into the patient's mouth and against the aforementioned internal mouth surface.

4. A method according to claim 1, wherein:

the niacin is a disk of niacin that is inserted into the patient's mouth and against the aforementioned internal mouth surface.

5. A method according to claim 1, wherein:

the niacin is applied as a strip that is inserted into the patient's mouth and against the aforementioned internal mouth surface.

6. A method according to claim 1, wherein:

the niacin is applied as a powder that is inserted into the patient's mouth and against the aforementioned internal mouth surface.

7. A method according to claim 1, wherein:

the niacin is held against the internal mouth surface for at least ten minutes.

8. A method according to claim 1, wherein: the niacin is combined with a flavoring agent.

* * * * *